US005637075A

United States Patent [19]
Kikawada

[11] Patent Number: 5,637,075
[45] Date of Patent: Jun. 10, 1997

[54] APPARATUS FOR OBSERVING INSIDE OF BODY CAVITY

[75] Inventor: Toru Kikawada, Shizuoka-ken, Japan

[73] Assignee: Hamamatsu ENT Surgicenter, Shizuoka-ken, Japan

[21] Appl. No.: 428,407

[22] Filed: Apr. 25, 1995

[30] Foreign Application Priority Data

Apr. 25, 1994 [JP] Japan ................................. 6-086300

[51] Int. Cl.$^6$ ........................................................ A61B 1/12
[52] U.S. Cl. ........................... 600/153; 600/105; 600/135; 600/156; 600/157; 604/43
[58] Field of Search ....................................... 600/105, 121, 600/123, 125, 135, 138, 153, 156, 158, 187, 203, 205, 157; 606/46; 604/27, 35, 43, 21, 902

[56] References Cited

U.S. PATENT DOCUMENTS

| | | |
|---|---|---|
| 4,517,962 | 5/1985 | Heckele . |
| 4,744,360 | 5/1988 | Bath ................................. 604/43 X |
| 4,881,523 | 11/1989 | Heckele . |
| 5,156,590 | 10/1992 | Vilmar ................................. 600/105 X |
| 5,386,817 | 2/1995 | Jones ................................. 600/157 X |

FOREIGN PATENT DOCUMENTS 6-67387  8/1994  Japan .

Primary Examiner—Richard J. Apley
Assistant Examiner—Beverly M. Flanagan
Attorney, Agent, or Firm—Lowe, Price, LeBlanc & Becker

[57] ABSTRACT

An apparatus for optically observing a body cavity in which the view field is made more clear by eliminating mucus in the body cavity. The apparatus includes a tubular fluid passage forming member which surrounds an insert part and which is inserted into the body cavity. A space between the fluid passage forming member and the outer face of the insert part is divided into a fluid supply space and discharge space. The fluid supply space is externally supplied with fluid such as clean water and the mucus in the body cavity is discharged to the outside of the body via the fluid discharge space. The fluid passage forming member is made of economical material such as plastics so that it may be disposable, reducing the risk of infecting a patient with a virus.

11 Claims, 9 Drawing Sheets

APPARATUS FOR OBSERVING INSIDE OF BODY CAVITY

DETAILED DESCRIPTION OF THE INVENTION

The present invention relates to an apparatus for observing the inside of a body cavity, and in particular to an apparatus for enabling the inside of the body cavity to be clearly viewed when an endoscope is inserted into the body cavity, such as nasal foramen, esophagus, stomach and large intestine, by eliminating pus, blood or mucus (or pituita) which blocks the view field when the endoscope is inserted into the body cavity to conduct an operation while observing the inside of the body cavity.

PRIOR ART

In recent years, nasal operations have been conducted for chronic sinusitis (empyema) to eliminate pus, excise mucosa of an inflamed part, and enlarge or provide an elimination opening by observing through an endoscope.

Specifically, the front end portion of the endoscope is inserted into the nasal foramen while an operator grips the endoscope by his or her left hand. The operation on the part to be operated on is carried out by the operator while gripping tweezers by his or her right hand.

When an observing system including an endoscope is used, the portion to be operated on, or an area in the vicinity thereof, is illuminated with light transmitted from a light source via a light guide. The light reflected on the illuminated area is transmitted through an objective lens, provided at a front end of an insert part of the endoscope, and is received by optical fibers in the insert part. The light transmitted through the optical fibers is observed via a view finder at the based end of the endoscope, or is image-processed so that it is displayed on an appropriate CTR display without the necessity of viewing via the view finder.

The present invention will be described in connection with an operation in nasal foramen for chronic sinusitis. Mucus, blood or pus (hereinafter referred to as mucus) exists in the nasal forame and is a contaminant for the endoscope in that it will block the view field. Blocking of the view field may result in the wrong portion being operated on with tweezers.

Accordingly, it is necessary to conduct an operation after the mucus has been eliminated to provide a clear view field. To this end, whenever the view field is blocked, a suction tube is inserted into the nasal foramen to eliminate the mucus via the tube.

The work required to remove the endoscope, insert the suction tube into the nasal foramen via a small opening, and to re-insert the endoscope after cleaning the inside of the nasal foramen will extend the period of time which is required to conduct the operation. There is also the risk that peripheral tissue may be damaged when the suction tube is inserted to a position where mucus exists or when the mucus is eliminated. In addition, it is necessary to wipe away the contaminant when it is deposited on the objective lens.

Laser treating methods have been conducted, and one method comprises inserting optical fibers into a treating instrument insert channel of an endoscope, directing a laser light from the base end of the optical fibers and irradiating a target part with the laser light emitted from the front end of the optical fibers. Japanese Examined Patent Publication No. Tokko Hei 6-67387 discloses that a tube is coaxially provided in the insert channel, the optical fibers are inserted into the tube, and pressurized air is pumped through the tube and discharged through the space between the tube and the insert channel to evacuate foreign matter or mucus which has been scattered from the irradiated part, outside of the body.

However, the tube can not be removed since it is integral with the endoscope. In order to prevent an infection by a virus such as hepatitis B virus or AIDS virus, it is necessary to disinfect the endoscope whenever it is used. However, a long period of time and considerable labor is required to wash the endoscope. If the disinfection is incomplete, there remains the risk of virus infection.

U.S. Pat. Nos. 4,517,962 and 4,881,523 disclose that liquid is supplied to a body cavity while the liquid, in the body cavity, is discharged. In these inventions, mucus or blood which is mixed with the discharged liquid, may remain since the same passage is used for both supply and discharge of the liquid. When a washing liquid is then supplied, the residual mucus or blood may be mixed with the washing liqui which will contaminate the target part to be observed, obscuring the view field.

Furthermore, it is necessary that the entire endoscope be disinfected after completion of the operation. In particular, it is necessary to carefully disinfect thin passages for the washing liquid and discharged liquid. If the disinfection is incomplete, the risk of viral infection remains.

Accordingly, in any of the above mentioned art, it is necessary to completely disinfect the endoscope used for each patient since the member forming the fluid flowing passage is not disposable. However, the risk of viral infection remains. In addition, the effect of washing on the objective lens is so inadequate that it is hard to clearly view the target portion.

SUMMARY OF THE INVENTION

It is, therefore, an object of the present invention to provide an observing apparatus for providing a clear view field by forcefully eliminating the mucus in a body cavity.

It is another object of the present invention to prevent patients from being infected with a virus by supplying a clear liquid into a body cavity to eliminate the mucus in the body cavity and to replace it the clear liquid and by making a member, forming a clear liquid passage, disposable.

The other objects and advantages will become more apparent from the following description.

In a first aspect of the present invention, there is provided an apparatus for optically observing the condition in a body cavity from outside of the body, including a main part located external to the body, and an insert part to be inserted into the body cavity from the outside, characterized in that the apparatus comprises a light transmitting member at the front end of the insert part which is positioned directly within the body cavity for transmitting a light from the body cavity;

an optical transmitting path for providing, outside of the body, optical information which is transmitted through the light transmitting member formed in the insert part and the main part; and a tubular fluid passage forming member which surrounds the outer periphery of the insert part and is detachably mounted on the insert part;

a space between the fluid passage forming member and the outer surface of the insert part being divided into a fluid supply space and a fluid discharge space which are in communication with the outside and the body cavity;

the fluid supply space being in communication with fluid supply means for introducing the fluid from outside of the body to the body cavity;

the fluid discharge space being in communication with fluid discharge means for discharging the fluid within the body cavity, together with contaminating liquid therein, outside of the body, An outlet of the fluid supply space and an inlet of the fluid discharge space are open in the vicinity of one side and the opposite side of the light transmitting member respectively. The fluid passage forming member is preferably disposable.

When the insert part is flexible, the fluid passage forming member may be made of a flexible plastic material or rubber. The insert part may be substantially circular in cross section on the outer periphery thereof, and the fluid passage forming member may be made of a deformable material and is substantially elliptical in cross section. The fluid passage forming member may be deformed when it is mounted on the outer periphery of the insert part so that small diameter portions of the fluid passage forming member are in close contact with the outer periphery of the insert part for dividing a space between the fluid passage forming member and the outer periphery of the insert part into a fluid supply and discharge spaces.

The fluid passage forming member may be formed with a plurality of dividing projections projecting from the inner wall thereof in angularly spaced relationship in a peripheral direction. The dividing projections may be in close contact with the insert part to divide a space between the fluid passage forming member and the insert part into a fluid supply and discharge spates.

In a second aspect of the present invention, there is provided an apparatus for optically observing the condition in a body cavity from outside of the body, including a main part located external to the body and an insert part to be inserted into the body cavity from outside of the body characterized in that the apparatus comprises a light transmitting member at the front end of the insert part which is positioned directly within the body cavity for transmitting a light from the body cavity;

an optical transmitting path for providing, outside of the body, optical information which is transmitted through said light transmitting member formed in the insert part and the main part; and a tubular fluid passage forming member which surrounds the outer periphery of the insert part and is detachably mounted on the insert part; and an adapter at the base portion of the insert part is not inserted into the body cavity and is positioned external to the body;

the adapter being formed with fluid supply and discharge passages which are defined between the inner periphery of the adapter and the outer periphery of the insert part;

a space between the fluid passage forming member and the outer surface of the insert part being divided into a fluid supply space and a fluid discharge space which are in communication with the outside and the body cavity; the base portion of the fluid passage forming member being adapted to the outer periphery of the adapter to cover the same;

the fluid supply space being supplied with fluid being in communication with fluid supply means for introducing the fluid from the outside to the body cavity; the fluid discharge space being in communication with fluid discharge means for discharging the fluid within the body cavity together with contaminating liquid therein to the outside, the fluid discharge opening of the fluid supply passage being open in the vicinity of the light transmitting member.

The light transmitting member is a lens. The main part includes a view finder. The lens may be optically linked with the view finder via optical fibers.

Optical fibers which guide the light condensed by the lens to the outside may be inserted into the insertion part so that optical information transmitted through the optical fibers is displayed as an image on an external display means.

The fluid discharge means may be driven by a vacuum pressure.

DESCRIPTION OF PREFERRED EMBODIMENT

The present invention will become more clear by reading the following description of the preferred embodiment with reference to the drawings.

The apparatus for observing the inside of a body cavity of the present invention comprises an optical observing means including a main part of an endoscope, and a system for supplying cleaning liquid and for discharging the mucus in the body cavity.

Figure 1:
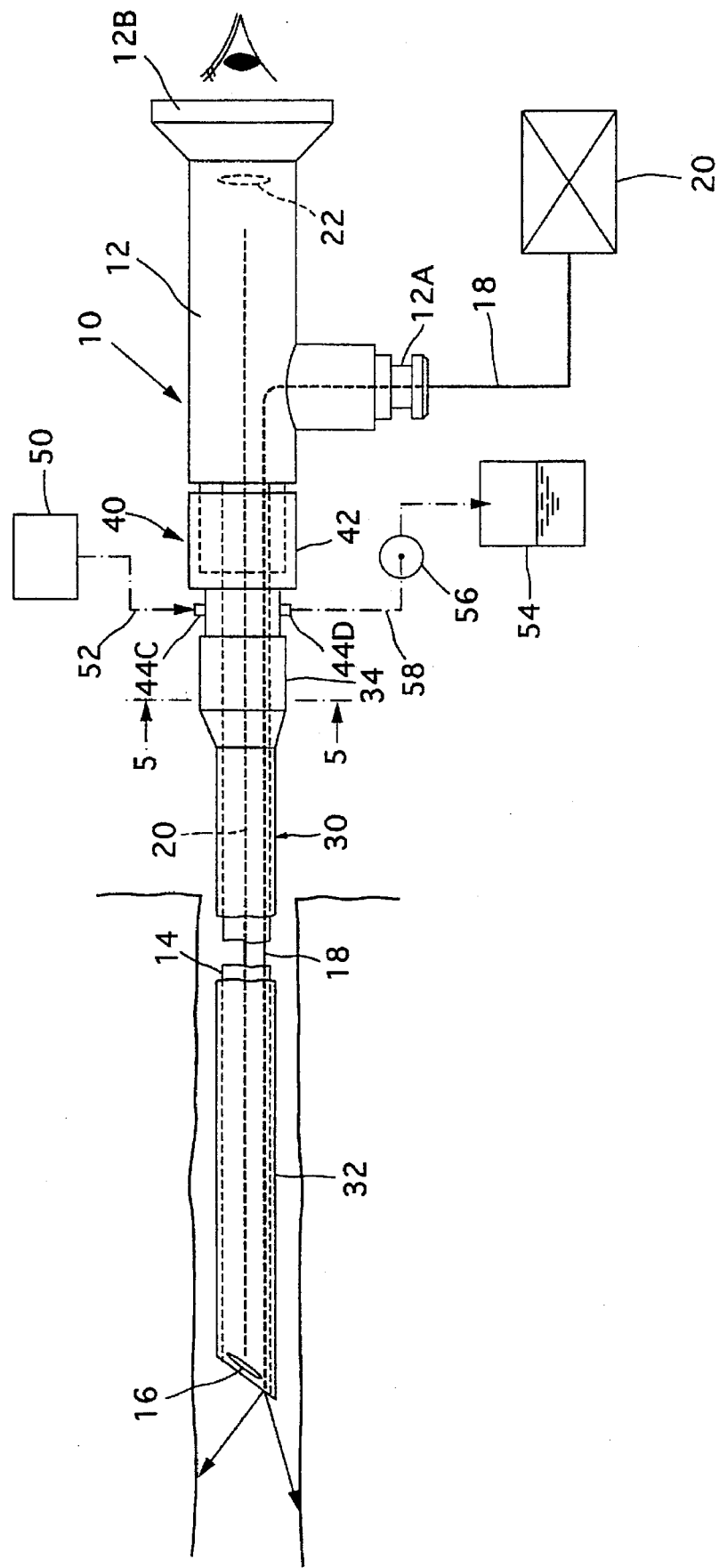
FIG. 1 is a schematic view showing the whole of an observing apparatus provided in a first aspect of the Invention.

FIG. 1 shows an endoscope used for nasal operations. The endoscope 10 has a main part 12 which is to be positioned external to a patient and an insert part 14 which is to be inserted into the body cavity of the patient from the outside. The insert part 14 is tapered at the front end to which an objective lens 16 is mounted. A light guide 18, including optical fibers, is inserted into an insertion hole 12A formed on a side of the main part 12. The light guide 18 extends through the insertion part 14 to the front end thereof. A light from a light source 20 is incident upon the light guide 18 and is then emitted from the front end of the light guide 18 toward a target portion for illuminating the same.

The light reflected on the target portion is incident upon the objective lens 16 to be focussed upon an image guide 20 which is a bundle of the optical fibers, and then transmitted through the image guide 20 and an eye piece lens 22. An operator is able to view the condition of the target portion via a view finder 12B.

A fluid passage forming member, made of, for example, flexible plastic material, is mounted around the outer periphery of the insertion portion 14. The passage forming member 30 has a guide portion 32 on the front end side and a close contact portion 34 on the base end side.

Figure 2:
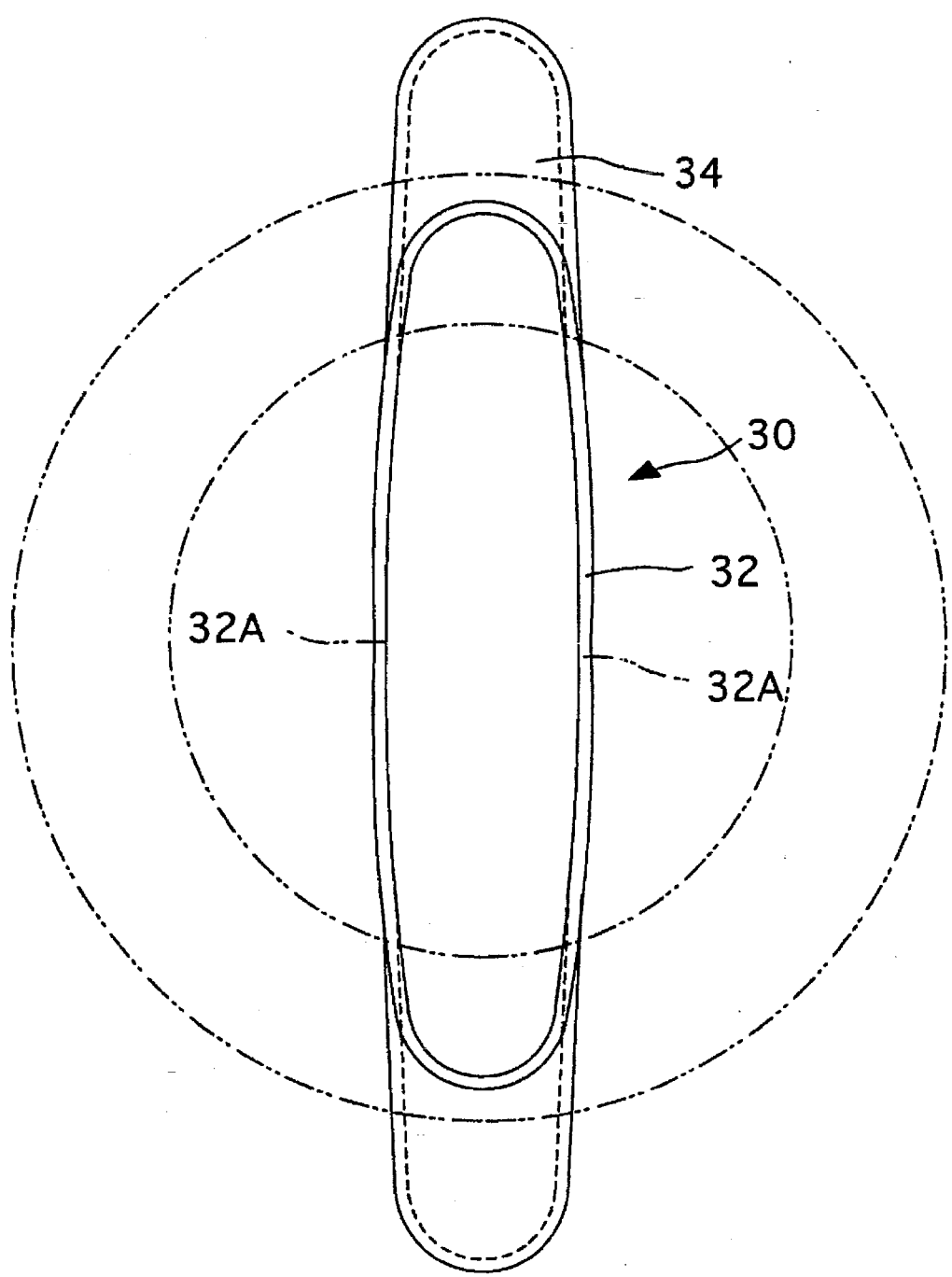
FIG. 2 is a left side view of a passage forming member which is not mounted on an endoscope.

The passage forming member 30 is elliptical in cross-section, as shown in FIG. 2, when the member 30 is not mounted on the main part 12.

Figure 3:
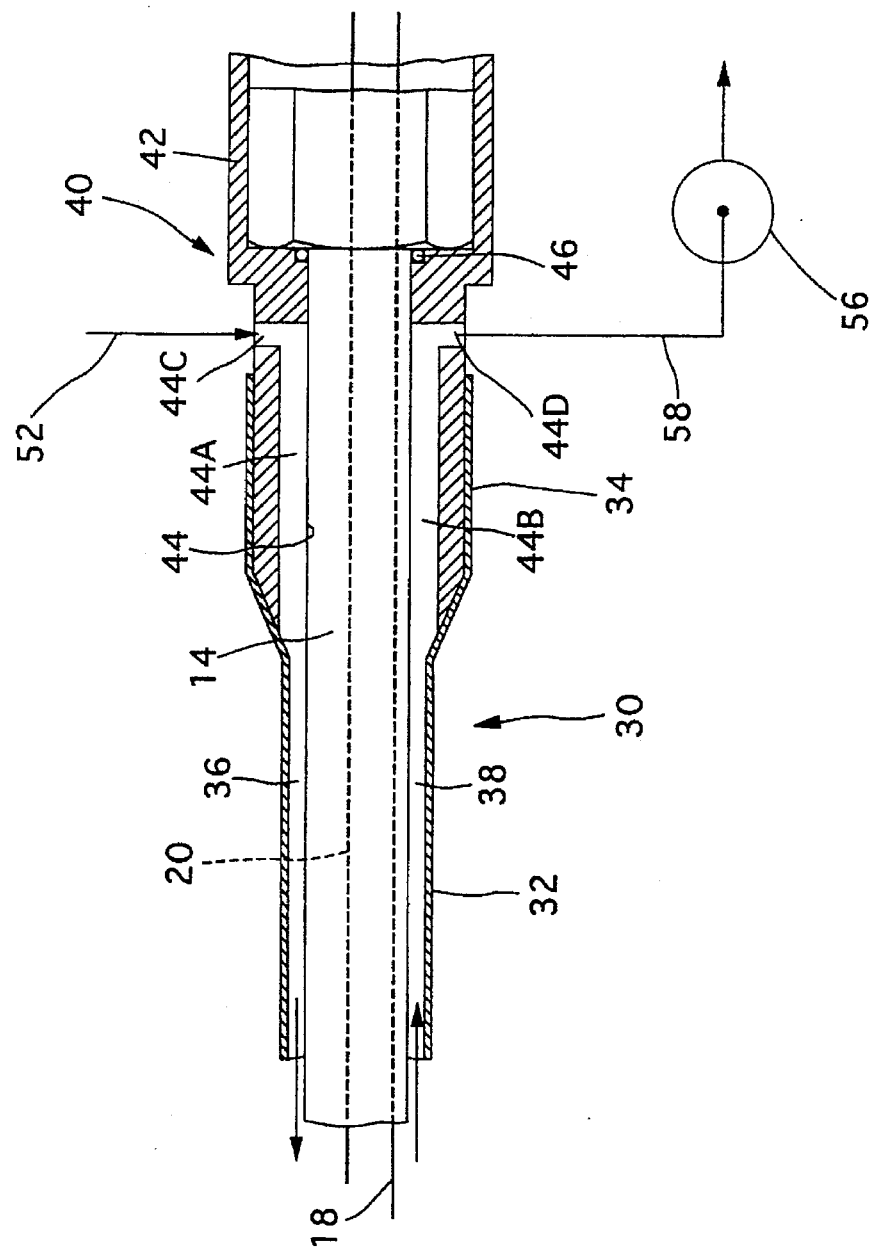
FIG. 3 is an enlarged longitudinal sectional view showing the apparatus of FIG. 1.

Referring to FIG. 3, a tubular adapter 40 is adapted as an interface portion between the base portion of the insertion part 14 and the main part 12. The adapter 40 has a larger diameter portion 42 on the base side, and is adapted to a hexagonal nut at the front end of the main part 12. The adapter 40 is formed with a supply guide passage 44A and with a discharge passage 44B at a 180° angular position with respect to the supply guide passage 44A and the position of the supply guide passage 44A and discharge passage 44B, can be changed by turning part of the insertion hole 44 in an axial direction. The supply and discharge guide passages 44A and 44B are opened on a front tapered face of the adapter 40 and radially extend through the wall of the adapter 40 so that they are in communication with an inlet 44C and outlet 44D, respectively. An interface between the adapter 40 and the insertion part 14 is sealed with an O-ring 46 to prevent supplied water from leaking.

On insertion of the passage forming member 30 onto the insertion part 14, the close contact portion 34 is deformed from the elliptical shape shown in FIG. 2 into the circular shape and in close contact with the entire outer periphery of the larger diameter portion 42 of the adapter 40 in a liquid tight manner as shown in FIGS. 3 to 6. The guide portion 32 is also adapted on the outer periphery of the insertion part 14 after it has been deformed from the elliptical shape to a substantially circular shape.

After the guide portion 32 has been adapted on the outer periphery of the insert part 14, only the small diameter portion of the elliptical shape is in close contact with the outer periphery of the insert part 14 and a space is formed between the larger diameter portion of the guide portion 32 and the outer periphery of the insert part 14 since the perimeter length of the outer periphery of the insert part 14 is made larger than the perimeter length of the inner periphery of the guide portion 32.

Figure 5:
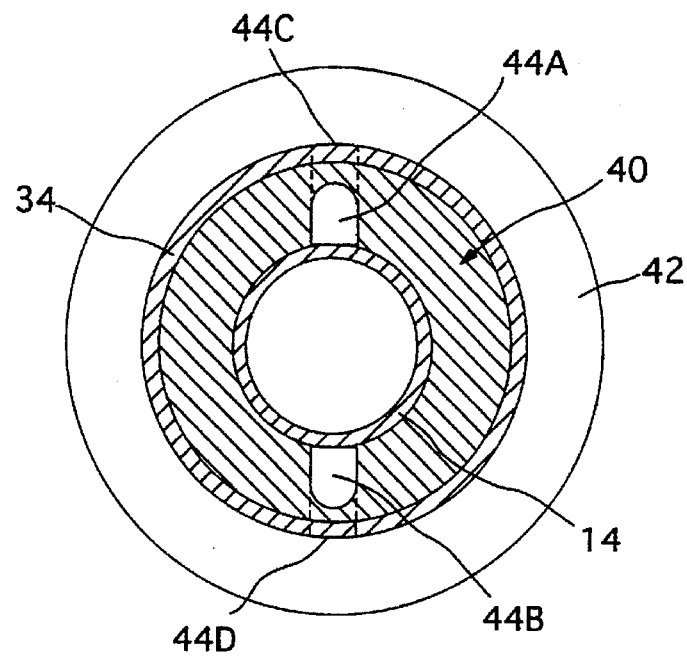
FIG. 5 is a view taken along a line 5—5 in FIG. 1.
Figure 6:
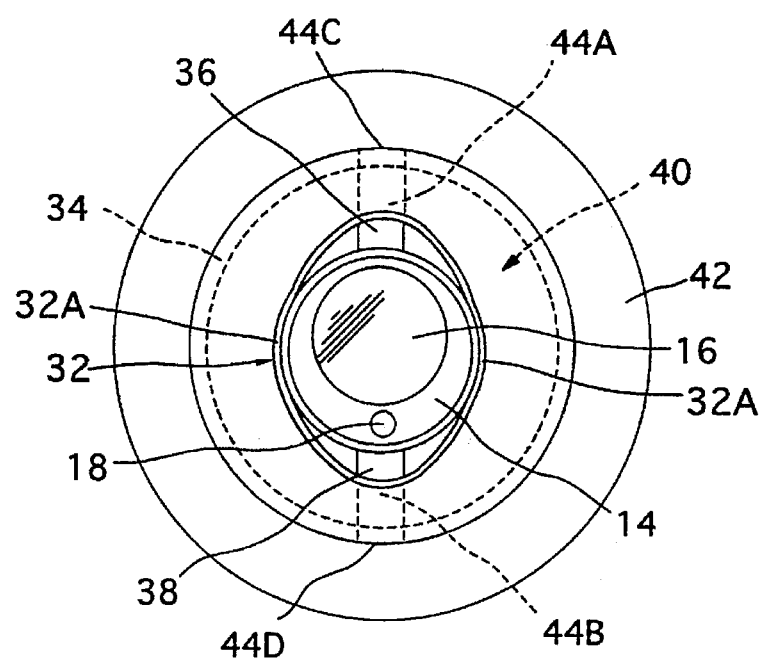
FIG. 6 is a left side view of FIG. 1.
Figure 7:
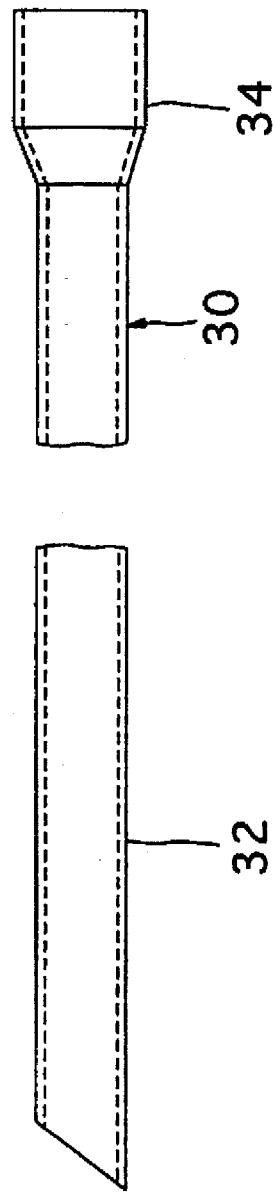
FIG. 7 is a front view showing a passage forming member.

As a result, the space between the guide portion 32 of the passage forming member 30 and the outer periphery of the insert part 14 is divided into a fluid supply passage 36 and fluid discharge passage 38 by the existence of the close contact areas 32A as clearly shown in FIGS. 5 and 6.

Figure 4:
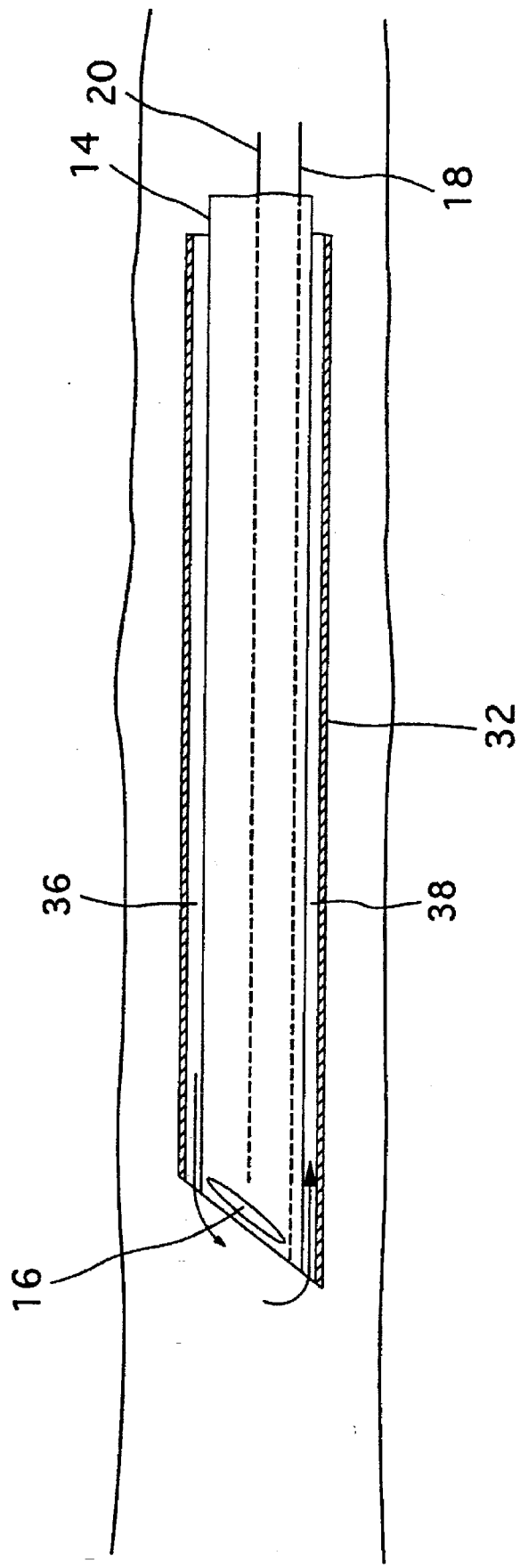
FIG. 4 is an enlarged longitudinal sectional view showing a main part of a front end portion of the apparatus.

The fluid supply passage 36 and fluid discharge passage 38 on the base side are in communication with the supply and discharge passages 44A and 44B, respectively as shown in FIG. 3. The front end of the guide portion 32 extends to, for example, the front end of the insert part 14. As a result, the fluid supply space 36 and the fluid discharge space 38 are open in the vicinity of one side and the opposite side of the objective lens 16, respectively, as shown in FIGS. 4 and 6.

On the other hand, as shown in FIG. 1, the inlet 44C is in communication with a reservoir 50 of physiological saline via a tube 52. The outlet 44D is in communication with a temporary disposal reservoir 54 via a pipe 58 having a vacuum pump 56 along the length thereof.

Endoscopes which are commercially available such as a rhinoscope or nasoscope may be used for nasal operation without conversion. Specifically, nasoscope, Model A7801-A7804 which is commercially available from Olympus Optical Co., Ltd. as one of NASAL SCOPE series may be used. The operator conducts a nasal operation while he or she views the target portion via the view finder 12B. The nasal operation may be conducted while viewing an image displayed on a TV monitor by using the nasoscope in combination with OES TV system OTV-S3/S4 by mounting an attachment of Olympus Optical Co., Ltd. on the view finder 12B if necessary.

When an operation for chronic sinusitis is conducted. the operator grips the endoscope by his or her left hand to insert the front end portion of the endoscope into the nasal cavity while gripping tweezers by his or her right hand.

When the target portion is observed through the endoscope, the target portion, or the area in the vicinity thereof, is illuminated with light from the light source 20 via the light guide 18. The light reflected from the illuminated area is received by the image guide 20 via the objective lens 16 which is provided at the front end of the insertion part of the endoscope and the illuminated area is viewed via the view finder 12B which includes an eye piece lens 22. Alternatively, a light signal incident upon the image guide 20 may be image-processed so that the image of the target portion displayed on an appropriate CRT display is observed without viewing through the view finder 12B.

In an operation in the nasal foramen, the mucus or pituita including blood and/or pus exists in the nasal cavity as contaminant for the endoscope so that the view field of the endoscope becomes restricted or blocked. Restriction of the view field may cause the operator to damage a portion, other than the target portion, with the tweezers.

Accordingly, if the mucus exists on the target portion, the mucus should be suctioned with vacuum pressure which is generated by starting the vacuum pump 66. The mucus is introduced through the fluid discharge space 38, the discharge passage 44B and the pipe 58 to the reservoir 54 for collection. If a valve of the pipe 52 is opened at this time, the physiological saline from the reservoir 50 flows from the pipe 52 into the supply passage 44A and is introduced into the body cavity via the supply passage 44A. The introduced physiological saline is merged with the discharged flow and creeps down on the surface of the objective lens 16 from one side to the opposite side to clean the lens 16. The discharged mucus on the target portion can be replaced with the physiological saline. As a result, the target portion can be clearly viewed.

Cleaning is accomplished each time that a necessity for cleaning occurs. After completion of the operation, the endoscope is removed from the nasal cavity together with the fluid passage forming member 30. After removal, the fluid passage forming member 30 is removed in a left direction as viewed in FIG. 1 for disposa and the endoscope is disinfected. For the next operation, a new fluid passage forming member 30 is adapted onto the insert part 14 of the disinfected endoscope.

Figure 8:
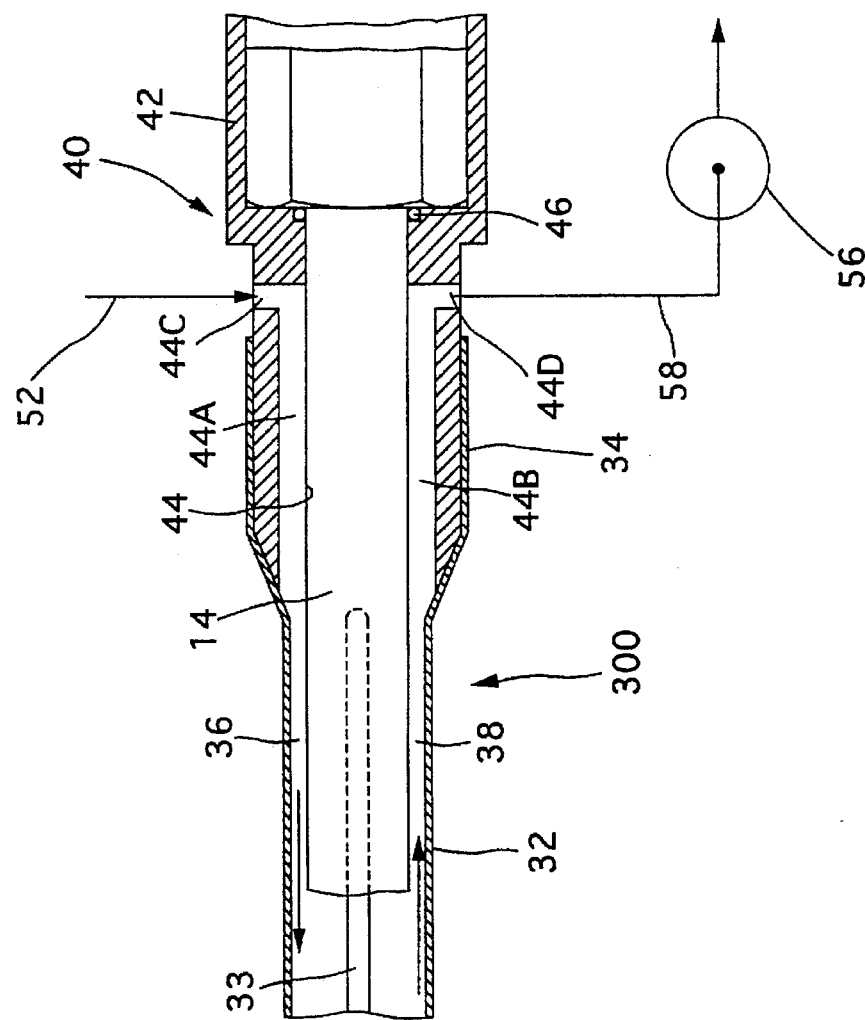
FIG. 8 is an enlarged longitudinal sectional view showing another embodiment.
Figure 9:
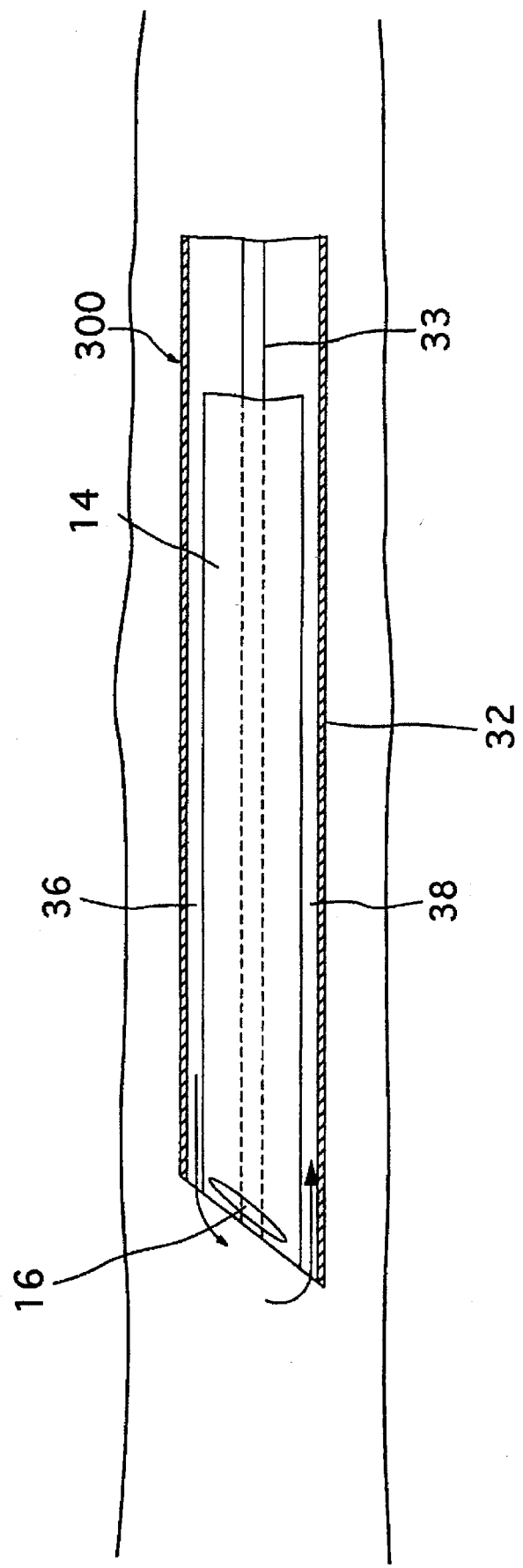
FIG. 9 is an enlarged longitudinal sectional view showing a front end portion of the apparatus.
Figure 10:
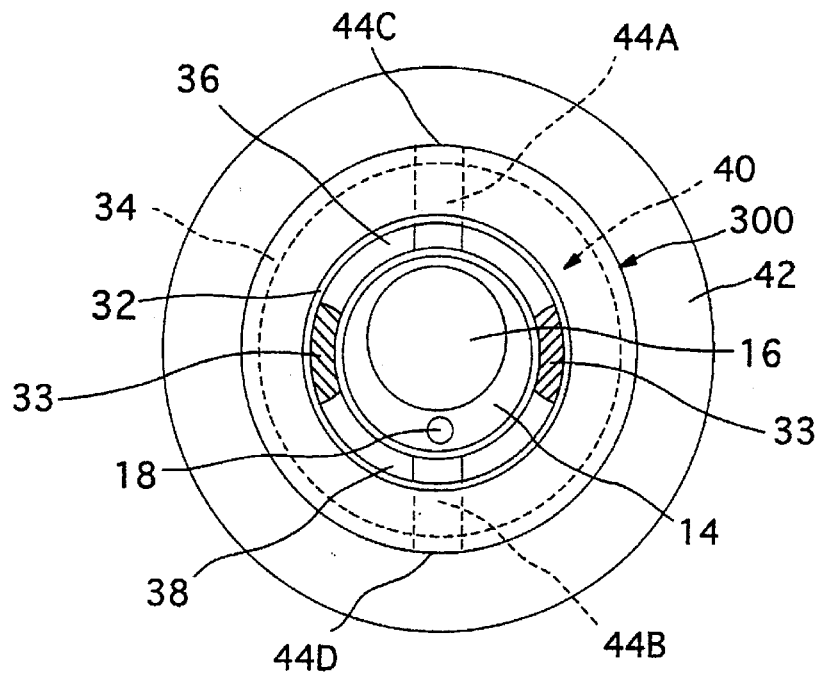
FIG. 10 is a left side view of FIG. 9.

The fluid passage forming member 30 has a substantially elliptical cross-section when it is not in use. An alternative fluid passage forming member 300 having an original circular cross-section, as shown in FIGS. 8 to 10, may be used. In this case, in order to divide the fluid passage, the fluid passage forming member 300 is formed on the inner surface thereof with axially extending dividing projections 33. The dividing projections 33 may be formed of the same material as that of the fluid passage forming member 300 when it is formed. The dividing projections may be integral with the fluid passage forming member 300. Existence of the dividing projections 33 enables the fluid supply space 36 and the fluid discharge space 38 to be divided.

Figure 11:
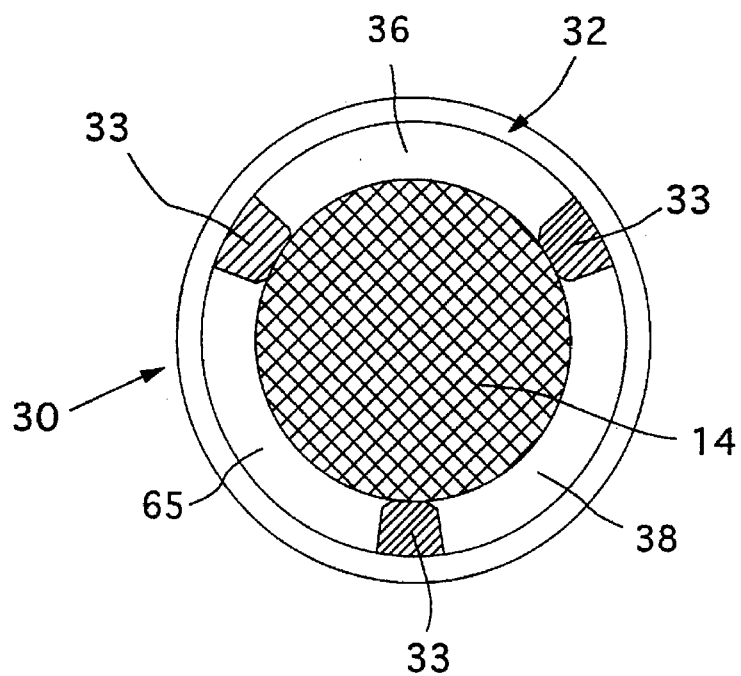
FIG. 11 is a cross sectional view of a further embodiment.

FIG. 11 shows a further embodiment of the invention in which the fluid supply space 36, the fluid discharge space 38 and an air supply space 65 are formed by dividing a space with three dividing projections 33.

In order to conduct a gallbladder removal operation, or a heart or lung operation using a laparoscope or thoracoscope, it is necessary to inflate the body cavity. To this end, air, such as carbon dioxide gas, can be supplied through the air supply space 65.

The apparatus for observing the inside of the body cavity of the present invention is applicable to a nasal operation as well as operations for other various body cavities. Although the present invention has been described with reference to the embodiment of the endoscope for the nasal operation, an endoscope having another structure may be used depending upon the operation and correspondingly, the structure of the fluid passage forming member may be changed.

Endoscopes having a rigid insert part, as well as those having a flexible insert part, may be used. In the case where the insert part is flexible, the flexible fluid passage forming member is, of course, used. The fluid passage forming member may be formed of various plastic materials including flexible plastic materials such as polyethylene, vinyl chloride, and polypropylene, and rigid plastic materials such as acrylic material, polycarbonate.

As mentioned above, in accordance with the present invention the view field can be made more clear by forcefully eliminating mucus in the body cavity. The view field can be also made more clear by supplying a cleaning liquid into the body cavity to eliminate the mucus and to replace it with the cleaning liquid. Infection of a patient with a virus can be prevented by making the fluid passage forming member disposable.

What is claimed is:

1. An apparatus for optically observing a condition in a body cavity from outside the body, including a main part to be located outside the body and an insert part to be inserted into the body cavity, said apparatus comprising:

a light transmitting member at a front end of said insert part which is to be positioned within said body cavity for transmitting a light to and from the body cavity;

an optical means extending from said main part to said insert part for providing light to the light transmitting member and optical information from said light transmitting member; and a tubular fluid passage forming member surrounding the outer periphery of said insert part and detachably mounted on the insert part;

a space between said fluid passage forming member and the outer surface of said insert part being divided into a fluid supply space and a fluid discharge space, said fluid supply space and fluid discharge space communicating between the body cavity and the outside;

said fluid supply space being coupled to a fluid supply means for introducing a fluid to said body cavity from the outside;

said fluid discharge space being coupled to a discharge means for discharging the fluid within said body cavity together with contaminated liquid therein to the outside;

an outlet of said fluid supply space and an inlet of said fluid discharge space being open in the vicinity of one side and the opposite side of said light transmitting member, respectively.

2. The apparatus according to claim 1 wherein said fluid passage forming member is disposable.

3. The apparatus according to claim 1 wherein said insert part is flexible and said fluid passage forming member is made of a flexible plastic material or rubber.

4. The apparatus according to claim 1 wherein said fluid passage forming member is formed with a plurality of dividing projections projecting from an inner wall thereof in an angularly spaced relationship in a peripheral direction, said dividing projections being in close contact with said insert part to divide a space between said fluid passage forming member and said insert part into a fluid supply space and discharge space.

5. An apparatus for optically observing the inside of a body cavity comprising:

an insert part having a substantially circular cross section on an outer periphery thereof; and a fluid passage forming member to be mounted on the outer periphery of said insert part and made of a deformable material, said fluid passage forming member including small diameter portions and having a substantially elliptical cross section, said fluid passage forming member being deformed when it is mounted on the outer periphery of said insert part so that the small diameter portions of said fluid passage forming member are in close contact with the outer periphery of said insert part, dividing a space between the fluid passage forming member and the outer periphery of the insert part into a fluid supply space and discharge space.

6. An apparatus for optically observing a condition in a body cavity from outside the body, including a main part to be located outside the body and an insert part to be inserted into the body cavity, said apparatus comprising:

a light transmitting member at a front end of said insert part which is to be positioned within said body cavity for transmitting a light to and from the body cavity;

an optical means extending from said main part to said insert part for providing light to the light transmitting member and optical information from said light transmitting member; and a tubular fluid passage forming member surrounding the outer periphery of said insert part and detachably mounted on the insert part; and an adapter at a base portion of said insert part which is not inserted into the body cavity;

said adapter being formed with fluid supply and discharge passages defined between an inner periphery of the adapter and the outer periphery of said insert part;

a space between said fluid passage forming member and the outer surface of said insert part being divided into a fluid supply space and a fluid discharge space each communicating between the body cavity and the outside;

a base portion of said fluid passage forming member being connected to and covering the outer periphery of said adapter;

said fluid supply space being supplied with a fluid from a fluid supply means for introducing said fluid to said body cavity from the outside;

said fluid discharge space being coupled to a fluid discharge means for discharging the fluid within said body cavity, together with contaminated liquid therein, to the outside, an outlet of said fluid supply space and an inlet of said fluid discharge space being open in the vicinity of one side and the opposite side of said light transmitting member, respectively.

7. The apparatus according to claim 6 wherein said light transmitting member is a lens.

8. The apparatus according to claim 6 wherein said optical means includes a view finder.

9. The apparatus according to claim 6 wherein said light transmitting member is a lens, said optical means includes a view finder, and said lens is optically linked with the view finder via optical fibers.

10. The apparatus according to claim 6 wherein said light transmitting member is a lens and said optical means includes optical fibers for guiding the light condensed by said lens to the outside and a display means for displaying the optical information transmitted through said optical fibers.

11. The apparatus according to claim 6 wherein the fluid discharge means is driven by vacuum pressure.

* * * * *